United States Patent [19]

Acton et al.

[11] Patent Number: 4,591,637

[45] Date of Patent: May 27, 1986

[54] OPEN CHAIN-MORPHOLINO ADRIAMYCINS

[75] Inventors: Edward M. Acton, Menlo Park; George L. Tong, Cupertino, both of Calif.

[73] Assignee: SRI International, Menlo Park, Calif.

[21] Appl. No.: 692,664

[22] Filed: Jan. 17, 1985

[51] Int. Cl.[4] .......................................... C07H 15/24
[52] U.S. Cl. ............................................... 536/6.4
[58] Field of Search ........................ 536/6.4; 424/180

[56] References Cited

U.S. PATENT DOCUMENTS

| | | | |
|---|---|---|---|
| 4,177,264 | 12/1979 | Wu et al. | 536/6.4 |
| 4,250,303 | 2/1981 | Wu et al. | 536/6.4 |
| 4,464,529 | 8/1984 | Mosher et al. | 536/6.4 |
| 4,477,444 | 10/1984 | Suarato et al. | 536/6.4 |

Primary Examiner—Johnnie R. Brown
Assistant Examiner—Elli Peselev
Attorney, Agent, or Firm—Ciotti & Murashige

[57] ABSTRACT

Compounds of the formula

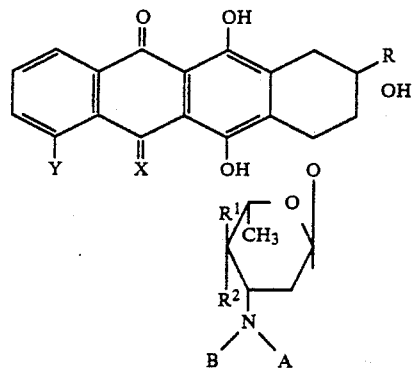

and the pharmaceutically acceptable salts thereof wherein R is:
—CO—CH$_3$, —CHOH—CH$_3$, —CO—CH$_2$OH, —CHOH—CH$_2$OH, hydrogen, hydroxy, 1 to 3 carbon alkyl, 1 to 3 carbon terminal hydroxyalkyl; or,
a 2 to 7 carbon ester or diester of said —CO—CH$_2$OH, —CHOH—CH$_2$OH, —CHOH—CH$_3$ or of said 1 to 3 carbon terminal hydroxyalkyl; or
said —CO—CH$_2$OH, —CHOH—CH$_2$OH, or —CHOH—CH$_3$ or said 1 to 3 C-terminal hydroxyalkyl having 1 to 6 carbon alkyl or aryl ether replacements of one or more of the hydroxyls; or
the 13-ketimine derivatives of —CO—CH$_3$ and —CO—CH$_2$OH;
Y is hydrogen, hydroxy, or methoxy,
X is O or NH, but when Y is hydrogen or hydroxy, X must be O;
at least one of R$^1$ and R$^2$ is hydrogen and the other is hydrogen, hydroxy, or methoxyl;
B is H, alkyl or optionally substituted aryl lower alkyl, said alkyl or optionally substituted aryl lower alkyl also optionally containing hydroxy, alkoxy, carbonyl, cyano or ester group substitutions; or
B and R$^2$ taken together, in order, are the methyleneoxygen bridge —CH$_2$—O—; and
A is —CHR$^3$CN wherein R$^3$ is H, optionally substituted aryl, alkyl or optionally substituted aryl lower alkyl, said alkyl or optionally substituted aryl lower alkyl optionally containing hydroxy, alkoxy, carbonyl, or ester group substitutions
are disclosed. These compounds are useful anti-tumor agents.

5 Claims, No Drawings

OPEN CHAIN-MORPHOLINO ADRIAMYCINS

TECHNICAL FIELD

The invention relates to providing compounds useful in chemotherapeutic treatment of tumors. In particular, it relates to analogs of doxorubicin and daunorubicin useful as chemotherapeutic agents.

BACKGROUND ART

A wide variety of anti-metabolites and other compounds have been used in chemotherapy for the treatment of malignancies in humans, with unpredictable records of failure and success. A number of compounds, such as 5-fluorouracil, adriamycin, cytoxan, and prednisone have been extensively used, and a number of other compounds have been shown to exhibit anti-tumor activity. It is understatement to acknowledge that a completely and predictively satisfactory chemotherapeutic agent has not been found. Those compounds currently employed are successful in some cases and not in others, and frequently, if not usually, involve side-effects which range from unpleasant to life-threatening. Accordingly, new compounds with anti-tumor activity, which also may have reduced toxicity, are always of interest.

The variability of effectiveness associated with the nature of the particular disease, and the metabolism of the treated subject, is a result of causes sufficiently obscure, that it appears probable there will be no universally effective single chemotherapeutic agent. Therefore, the interests of the population needing treatment as a whole are best served by providing a spectrum of agents which have the required activity, and exhibit individual differences in metabolic effects.

Adriamycin is a generic name for doxorubicin which, along with its 14-deoxy analog, daunorubicin, is a successful agent in the treatment of a large number of solid tumors and leukemias. Typically, however, the success of specific compounds in this class is not uniform with respect to all patients, and the rate of success is lower with some particular tumor types, such as colon cancer and melanoma. Side effects of treatment with doxorubicin and daunorubicin include damage to the cardiovascular system and symptomatic distress. Thus, a number of analogs to these compounds have been prepared, which are active in a standard screen against mouse leukemia P-388, and exhibit variation in level of side-effects and mode of action.

Summaries of the spectrum of analogs currently available are found in Henry, D. W., *Adriamycin*, ASC Symposium Series No. 30, Cancer Chemotherapy, American Chemical Society (1976) 15-57; and in Arcamone, F., *Doxorubicin*, Academic Press, (1981). One analog under trial, AD32, is disclosed in U.S. Pat. No. 4,035,566.

A number of other analogs have been disclosed. U.S. Pat. No. 4,109,076 discloses 5-imino-daunorubicin; its doxorubicin analog is disclosed in Acton, E. M., et al, *J Med Chem* (1981) 24:669. U.S. Pat. No. 4,301,277 discloses the morpholino analog of daunorubicin, 3'-deamino-3'-(4"-morpholino)daunorubicin; additional analogs of this compound and their properties, as well as those of the 4-methoxy-1-piperidinyl analog, are disclosed in Mosher, C. W., et al, *J Med Chem* (1982) 25:18-24. 3'-N-alkylated analogs are disclosed in Tong, G. L., et al, *J Med Chem* (1979) 22:912-918. The N-benzyl and N,N-dibenzyl derivatives are disclosed in U.S. Pat. Nos. 4,177,264 and 4,250,303.

U.S. Pat. No. 4,464,529 discloses additional morpholino analogs bearing a cyano group in the 3-position of the morpholine ring. A continuation-in-part of the original application, upon which the foregoing patent is based, Ser. No. 598,016, filed Apr. 9, 1984, and assigned to the same assignee, incorporated herein by reference, discloses additional permutations of the morpholino-type derivatives of adriamycin-like compounds.

DISCLOSURE OF THE INVENTION

The present invention provides additional compositions of matter in the repertoire of useful chemotherapeutic agents of the adriamycin family. In the compounds of the present invention, the adriamycin analogs represent, in general, open chain analogs of the morpholino derivatives described in the above referenced copending application.

Specifically this invention relates to compounds of the formula

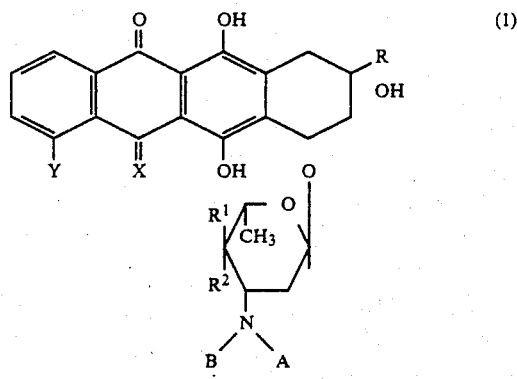

and the pharmaceutically acceptable salts thereof wherein R is:
- —CO—CH$_3$, —CHOH—CH$_3$, —CO—CH$_2$OH, —CHOH—CH$_2$OH, hydrogen, hydroxy, 1 to 3 carbon alkyl, 1 to 3 carbon terminal hydroxyalkyl; or,
- a 2 to 7 carbon ester or diester of said —CO—CH$_2$OH, —CHOH—CH$_2$OH, —CHOH—CH$_3$ or of said 1 to 3 carbon terminal hydroxyalkyl; or
- said —CO—CH$_2$OH, —CHOH—CH$_2$OH, or —CHOH—CH$_3$ or said 1 to 3 C-terminal hydroxyalkyl having 1 to 6 carbon alkyl or aryl ether replacements of one or more of the hydroxyls; or
- 13-ketimine derivatives of —CO—CH$_3$ and —CO—CH$_2$OH, such as oximes or hydrazones, Y is hydrogen, hydroxy, or methoxy, X is O or NH, but when Y is hydrogen or hydroxy, X must be O;

at least one of $R^1$ and $R^2$ is hydrogen and the other is hydrogen, hydroxy, or methoxy;

B is H, alkyl or optionally substituted aryl lower alkyl, said alkyl or optionally substituted aryl lower alkyl also optionally containing hydroxy, alkoxy, carbonyl, cyano or ester group substitutions; or B and $R^2$ taken together, in order, are the methylene-oxygen bridge —CH$_2$—O—; and A is —CHR$^3$CN wherein $R^3$ is H, optionally substituted aryl, alkyl or optionally substituted aryl lower alkyl, said alkyl or optionally substituted aryl lower alkyl optionally containing hydroxy, alkoxy, carbonyl, or ester group substitutions.

The compounds of formula 1 are analogs of the established anti-tumor drugs daunorubicin and doxorubicin, and are prepared from them by chemical derivatization techniques. The compounds of formula 1 are active anti-tumor agents, and have patterns of dosage levels and ancillary effects which are complementary to those exhibited by doxorubicin and daunorubicin per se.

In other aspects, the invention provides pharmaceutical compositions containing the new compounds of formula 1, and relates to a method for treating mammalian tumors by administering these preparations.

MODES OF CARRYING OUT THE INVENTION

A. Definitions

The compounds of the invention may carry optionally substituted aryl, alkyl, or aryl lower alkyl substituents. "Alkyl" as used herein refers to a straight or branched chain saturated hydrocarbon which contains 1-6 carbons unless otherwise specified. Exemplary are methyl, ethyl, propyl, isobutyl, isopentyl, and hexyl. Optionally substituted "aryl" refers to phenyl, or other aryl groups, such as pyridyl, furanyl, imidazolyl, and the like which may or may not be substituted with 1-3 substituents selected from halo, lower alkyl (1-4C), nitro, or lower alkoxy. "Optionally substituted aryl lower alkyl" refers to a moiety in which the aryl group is attached to the relevant atom of the compound by an intervening lower (1-4C) alkyl. Exemplary are benzyl, phenylethyl, 2-(4-fluorophenyl)ethyl, 3-(3,5-dimethylphenyl)-n-propyl and so forth. Analogous aryl lower alkyl embodiments contain heterocyclic aromatic groups such as pyridyl or imidazolyl in place of phenyl. Where the "optionally substituted aryl lower alkyl" is said, itself to "optionally contain" additional substitutions, these substitutions are present on the alkyl portion of the substituent. In that regard, "alkoxy" refers to RO—, carbonyl is —COR, and ester group substituents are —COOR, all wherein R is alkyl as herein defined.

Ketimine derivatives refer to derivatives of carbonyl which have the formula C=NK, wherein K is OH, or NHS, wherein S is H, $CONH_2$, acyl, alkyl, or optionally substituted phenyl.

It is to be noted that the compounds of the invention have greatly diminished basicity due to the presence of the α-cyano in substituent A, and, in some embodiments, other electron withdrawing groups in the A or B substituent. However, to the extent the compounds of the invention retain weak basicity sufficient to generate, when properly reacted, the acid addition salt, the resulting salts are included in the compounds of the invention.

Any of the compounds of the invention which can be prepared as the pharmaceutically acceptable acid addition salts are convertible to compounds soluble in water and aqueous mixed solvents such as water/alcohols or water/alkane diols. The free bases are soluble in less polar organic solvents such as chloroform, methylene chloride, and mixtures thereof. "Pharmaceutically acceptable acids" used to prepare the salts are non-toxic and generally employed in pharmaceutical products, for example hydrochloric, hydrobromic, phosphoric, acetic, glycolic, maleic, tartaric, citric, and organosulfonic acids such as methane sulfonic and para-toluene sulfonic acids.

The compounds of the invention may contain one or more chiral centers wherein the configuration is unspecified, in addition to the chiral centers of specified configuration as shown in Formula 1. These compounds, therefore, exist in diastereomeric forms, which may be separated using conventional techniques such as chromatography, selective crystallization and so forth.

B. Preparation Methods

The compounds of the invention may be prepared by using direct nucleophilic substitution with the iodoacetonitrile derivatives to obtain substituted N-cyanomethyl derivatives. However, this approach is inferior to using the Zelinsky-Stadnikoff modification of the Strecker amino acid synthesis (*Merck Index* 1984, ONR-87). The general aspects of this synthesis are shown in Reaction Scheme 1;

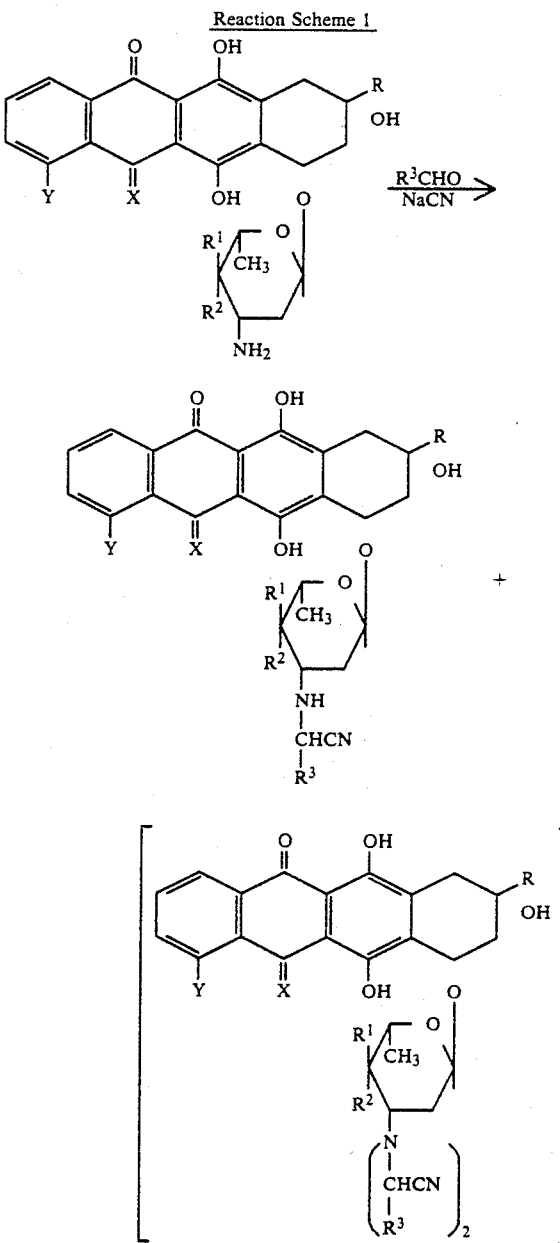

wherein $R^3$ is as above defined. Conditions employed in such amination-cyanation reactions of aldehydes are set forth in Cavalleri, B., et al, *J Med Chem* (1977) 20:1552.

The di-substituted analogs are formed as by-products of the reaction in Scheme 1, and the symmetrically substituted N,N-di-α-cyano compounds of the invention are prepared by extending the reaction times employed, and increasing the concentration of reagents.

The unsymmetrical di-substituted products are prepared by reaction with the appropriate reactive alkyl iodide, preferably prior to, but permissibly subsequent to the substitution with the α-cyano containing CHR$^3$CN group of A. If B also contains α-cyano, but is not identical with A, substitution with both A and B may be carried out.

C. Utility and Administration

The anti-tumor activity of the compounds of formula 1 is evidenced by in vivo and in vitro studies. An in vivo test is conducted as described in *Cancer Chemotherapy Reports, National Cancer Institute*, 3, No. 2, Part 3, September, 1972. Healthy mice are inoculated IP with lymphocyte leukemia P-388 ascitic fluid, and then treated on days 5, 9 and 13 of the succeeding period with various amounts of compounds of the invention. Untreated mice, and mice treated with daunorubicin, or doxorubicin were used as controls. Survival times and % T/C (treated survival time/untreated survival time × 100) were determined, as well as dosage levels required.

An in vitro test measured inhibition of DNA and RNA synthesis in L-1210 Cells in the method described by Tong, G., et al, *J Med Chem* (1976) 19:395. ED$_{50}$ levels (the dose at which 50% inhibition occurs) were computed and ED$_{50}$ ratios for DNA/RNA determined. It has been suggested by Crooke, S. T., et al, *Mol Pharmacol* (1978) 14:290 that a high DNA/RNA ratio indicates improved therapeutic properties.

Tests were run to verify the biological activity of compounds of this invention in vivo in mice against P-388 leukemia, L1210 leukemia and B-16 melanoma essentially by the method of the above-noted *Cancer Chemotherapy Reports*, 1972, using various dose schedules and IP, IV and oral routes of administration.

Compounds of formula 1, including any salts thereof, can be administered by conventional routes, including oral and parenteral (intravenous, intraperiotoneal, subcutaneous, and intramuscular) administration, preferably by intravenous administration. The dose regimen and amount administered depends on the subject and the nature of the malignancy. For example, in the treatment of murine test animals, about 0.5 mg/kg to about 50 mg/kg per day of the compound of formula 1 is sufficient to ameliorate leukemia. An upper dosage limit is imposed by toxic side effects and can be determined by trial and error for the animal to be treated. Regimens of one dose every 2 to 7 days are effective, as are shorter intervals of one day of less.

To facilitate administration, the compounds or their salts can be provided in pharmaceutical composition form, and particularly in unit dosage form. While the compounds can be administered per se, it is more common to administer them in conjunction with a pharmaceutically acceptable carrier which dilutes the compound and facilitates handling. The term "pharmaceutically acceptable" means that the carrier (as well as the resulting composition) is sterile and nontoxic.

For oral dosage, the carrier or diluent can be solid, semisolid, or liquid, and can serve as a vehicle, excipient, or medium for the agent as described in pharmacology texts. For parenteral administration, the compound is dissolved or suspended in a suitable injectable liquid medium as is known in the art.

In the preparation of these dosage forms, one can use the art accepted techniques for formulating water-soluble pharmaceutical agents (in the case of the free bases) and water-insoluble agents (in the case of free bases).

For example, injectable materials can be formulated as follows:

|  | mg |
| --- | --- |
| Active ingredient | 3 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Similarly, one could formulate tablets for oral administration as follows:

|  | mg |
| --- | --- |
| Active ingredient | 5.0 |
| Lactose | 91 |
| Cornstarch (dried) | 51.5 |
| Gelatin | 2.5 |
| Magnesium stearate | 1.0 |

(The active ingredient is powdered and passed through a mesh sieve and well mixed with the lactose and 30 mg of the cornstarch, both passed through a sieve. The mixed powders are massed with a warm gelatin solution, prepared by stirring the gelatin in water and heating to form a 10% w/w solution. The mass is granulated by passing through a sieve, and the moist granules dried at 40° C. The dried granules are re-granulated by passing through a sieve and the balance of the starch and the magnesium stearate is added and thoroughly mixed. The granules are compressed to produce tablets each weighing 150 mg.)

Capsules could be formulated as follows:

|  | mg |
| --- | --- |
| Active ingredient | 10 |
| Lactose | 190 |

(The active ingredient and lactose are passed through a sieve and the powders well mixed together before filling into hard gelatin capsules of suitable size, so that each capsule contains 200 mg of mixed powders.)

D. EXAMPLES

The following examples are intended to illustrate, but not to limit the invention.

EXAMPLE 1

Preparation of N-(cyanomethyl)daunorubicin (N-cyanomethylDau)

(A) Preparation of Nucleophilic Substitution

A sample of 0.017 grams (0.21 mmol) of anhydrous sodium acetate and 15 μl (0.033 g, 0.197 mmol) of iodoacetonitrile were added to a solution of 0.065 grams (0.123 mmol) of daunorubicin, free base, in 1 ml of dry DMF, and the dark red mixture thus obtained stirred at room temperature in the dark for 44 hours until thin layer chromatography (TLC) run on aliquots of the reaction mixture showed conversion to the desired product. The reaction mixture was then evaporated at low temperature and pressure (about 35°, <5 mm), the residue dissolved in 10 ml chloroform/methanol (9/1) and the solution washed with acetic acid, water, and sodium bicarbonate and dried. The organic layer was evaporated, and the residue further purified to obtain 0.059 g (84%) of the desired N-cyanomethylDau. Daunorubicin (0.010 g) was recovered from the acetic acid extract.

The majority of the material recovered from the organic phase was further purified to yield N-cyanomethylDau with a small amount of the bridged oxymethylene analog anhydro-N-cyanomethyl-N-hydroxymethylDau.

(B) Preparation with Formaldehyde-NaCN

A 200 μl (2.66 mmol) aliquot of 37% formaldehyde was added to a stirred solution containing 0.564 g (1.0 mmol) of daunorubicin-HCl in 15 ml of acetonitrile/water (2/1). This was followed by dropwise addition of a solution containing 0.130 g (2.66 mmol) of sodium cyanide in 3.3 ml (1.65 mmol) of 0.5N HCl. The solution was stirred at room temperature in the dark for an hour until TLC on aliquots of the mixture indicated that reaction was complete.

The reaction mixture was poured into 50 ml water, and the aqueous mixture extracted with chloroform. After washing, the chloroform was dried over sodium sulfate, filtered through celite, and evaporated. The residue was dissolved in 10 ml methylene chloride and the solution stirred while 40 ml of ether was added dropwise. The mixture was evaporated and the residue dried to obtain 0.539 g of a red semi-solid residue representing 95% yield of N-cyanomethylDau. TLC showed the residue to be slightly impure.

EXAMPLE 2

Preparation of N-(1-cyano-2-methoxyethyl)Dau

A solution containing 0.060 g (0.5 mmol) of methoxyacetaldehyde dimethylacetal in 0.8 ml of 0.5N HCl was heated at 50° for 30 min and cooled to room temperature. The freshly prepared methoxy acetaldehyde solution was added to a stirred suspension of 0.056 g (0.1 mmol) of daunorubicin HCl in 1 ml of acetonitrile, followed by addition of 0.2 ml of an aqueous solution containing 0.026 g (0.53 mmol) of sodium cyanide. The dark red solution obtained was stirred at room temperature in the dark for 4.5 hours, determined to be the reaction time by TLC. The mixture was then poured into 5 ml water, and extracted with chloroform. The chloroform extracts were washed as above, filtered, dried, evaporated, and redissolved in methylene chloride. Ether was added to turbidity, and the turbid mixture evaporated to dryness to give an impure semi-solid residue representing 0.047 g (77% yield of the desired product if pure). The product, N-(1-cyano-2-methoxyethyl)Dau, when subjected to 90 MHz NMR shows a pattern consistent with the desired product and a purity of approximately 75–85%, with 10–20% cyanohydrin and 5–10% of a by-product. A similar product, from an earlier preparation, was purified to obtain the desired N-(1-cyano-2-methoxyethyl)Dau. NMR on this material was consistent with the desired structure. UV-visible in methanol showed maxima at 234 nm, 252 nm, 289 nm, 489 nm, 496 nm, 530 nm.

The residue, subjected to HPLC, showed a mixture containing the desired material as the major product (often as two peaks, due to the chirality of the α carbon) with minor contaminants.

EXAMPLE 3

Preparation of N-(1-cyano-2-methoxyethyl)doxorubicin (N-(1-cyano-2-methoxyethyl)Dox)

The synthesis is analogous to that set forth in Example 2 for daunorubicin. Nine ml of a 0.5N HCl solution containing 0.601 g (5 mmol) of methoxyacetaldehyde dimethylacetal, was heated at 50° for 30 min, cooled to room temperature and added to a stirred suspension of 0.290 g (0.5 mmol) of doxorubicin HCl in 20 ml of acetonitrile, along with 6 ml of water. Following addition, 5 ml of an aqueous solution containing 0.245 g (5.0 mmol) of sodium cyanide were added, the dark red solution stirred at room temperature in the dark, and the reaction followed by TLC. After 5 hours, the reaction mixture was poured into water and the product recovered as in the previous examples. A gum having a mass of 0.235 g was obtained. Analysis by 90 MHz NMR in $CDCl_3$ is consistent with 30–40% of the desired product N-(1-cyano-2-methoxyethyl)Dox, 20–30% of its cyanohydrin, and 30–40% of various side products of the aldehyde.

Additional material (0.147 g) was recovered from the aqueous phase of the original extraction, and shown by 90 MHz NMR to contain 40–50% of desired product, 15–25% of its cyanohydrin, and 20–25% of the side products.

A 0.380 g sample of the combined foregoing crude mixture was dissolved in 10 ml of chloroform/acetone (1/1) and a trace (<0.0005 g) of sodium cyanide added. The turbid solution was stirred at room temperature in the dark for 15 hours. The reaction mixture was filtered through a millipore filter and the precipitate washed with chloroform/acetone and dried to afford a red powder of 0.004 g of a contaminant. The filtrate was evaporated and the residue dissolved in 5 ml of methylene chloride, and 25 ml of ether added dropwise with stirring. The resulting precipitate was collected and washed with ether to obtain 0.244 g of a dark red powder. Additional product was recovered from the filtrate.

The foregoing red powder and filtrate-recovered material were combined in 1.5 ml of methylene chloride/methanol (19/1) and applied to a silica gel column prepared from 16 g of Bio-Rad Bio-Sil-A 200–400 mesh, packed and washed with methylene chloride. Fractions containing products were combined and evaporated and the residue dissolved in methylene chloride, filtered through Celite, and evaporated. The residue was then dissolved in methylene chloride diluted with 5 vol of ether, and evaporated and dried, to yield 0.144 g of the desired product.

The 0.143 g of N-(1-cyano-2-methoxyethyl)Dox was triturated with 5 ml of ether and the precipitate (0.136 g) collected, washed and dried.

This product was submitted for C, H and N analysis, with the following results: calculated for $C_{31}H_{34}N_2O_{12} \cdot \frac{1}{2}H_2O$ (635.63): C: 58.58; H: 5.55; N: 4.41; found: C: 58.39; H: 5.67; N: 4.63. Mass spec gave an m/e apparent peak of 626 and HPLC results were consistent with approximately 92% purity. 300 MHz NMR was consistent with this level of purity in the desired product.

EXAMPLE 4

Preparation of N-(cyanomethyl), N-(ethoxycarbonylmethyl)daunorubicin

A solution was prepared containing 0.057 g (0.1 mmol) of N-cyanomethylDau as prepared in Example 2 in 1 ml of DMF. To this solution were added 0.008 g (0.1 mmol) of anhydrous sodium acetate and 25 μl (0.2 mmol) of ethyl iodoacetate. The dark red solution was stirred at room temperature in the dark for the course of reaction as determined by TLC. After 44 hours the reaction mixture was poured into 10 ml of water, and the product extracted with chloroform and recovered. The resulting gum was redissolved in methylene chloride and precipitated with ether to obtain 0.059 g of a red powder which was shown by 90 MHz NMR to be a mixture of 50–60% product, and 30–40% starting material. Additional products shown to be present by TLC include the corresponding lactone formed with the 4'-hydroxyl, and an anhydro product formed by the elimination of water from the hydrolyzed cyano derivative, containing the oxymethylene bridge to the 4' position of the sugar. Preparative TLC afforded the desired product in 70–80% purity as indicated by TLC, MS, and NMR analysis.

EXAMPLE 5

Conversion of the Ethoxycarbonyl Substituent to the Sodium Salt

A solution was prepared containing 0.065 g (about 0.075 mmol) of the impure N-cyano-N-(ethoxycarbonylmethyl)Dau from the previous example in 2 ml acetone. The solution was cooled to 20° and 1.6 ml of a 0.05N NaOH solution (0.08 mmol) was added dropwise. The blue-violet solution was stirred at room temperature in the dark and the reaction followed by TLC. After 30 minutes, the solution was diluted with 10 ml of water and then extracted with chloroform. The aqueous phase (pH 8.6) was filtered through celite and the filtrate frozen and lyophilized in the dark to obtain 0.039 g of a product of about 80% purity. This was a mixture of the sodium salts of the desired N-cyano-N-(ethoxycarbonylmethyl)Dau and N-(ethoxycarbonylmethyl)-Dau.

EXAMPLE 6

The following derivatives of daunorubicin or doxorubicin are also prepared using the procedures set forth above:

N-(α-cyanobenzyl)daunorubicin
N-(α-cyanobenzyl)doxorubicin (see also *J Org Chem* (1961) 26:4741; *J Pharmacol Exp Therapeutics* (1978) 205:751)
N-(1-cyano-2-phenylethyl)daunorubicin
N-(1-cyano-2-phenylethyl)doxorubicin
N-(1-cyano-2-benzoxyethyl)daunorubicin
N-(1-cyano-2-benzoxyethyl)doxorubicin
N-(1-cyano,(4-methoxyphenyl)methyl)daunorubicin
N-(1-cyano,(4-methoxyphenyl)methyl)doxorubicin
N-(1-cyano,(4-carboxylatophenyl)methyl)daunorubicin
N-(1-cyano,(4-carboxylatophenyl)methyl)doxorubicin
N-(1-cyano,4-pyridylmethyl)daunorubicin
N-(1-cyano,4-pyridylmethyl)doxorubicin
N-(1-cyano,(5-methoxyfuran-2-yl)methyl)daunorubicin
N-(1-cyano,(5-methoxyfuran-2-yl)methyl)doxorubicin
N-(1-cyano-2,3-dihydroxyprop-1-yl)daunorubicin
N-(1-cyano-2,3-dihydroxyprop-1-yl)doxorubicin
N-(1-cyano-2,3-dimethoxyprop-1-yl)daunorubicin
N-(1-cyano-2,3-dimethoxyprop-1-yl)doxorubicin
N-(1-cyano-3-methoxy-2-(methoxymethyl)prop-1-yl)daunorubicin
N-(1-cyano-3-methoxy-2-(methoxymethyl)prop-1-yl)doxorubicin
N,N-dicyanomethyldaunorubicin
N,N-dicyanomethyldoxorubicin
N,N-di-(1-cyano-2-methoxyethyl)daunorubicin
N,N-di-(1-cyano-2-methoxyethyl)doxorubicin
N-(cyanomethyl)-N-(benzyl)daunorubicin
N-(cyanomethyl)-N-(benzyl)doxorubicin
N-(1-cyano-2-methoxyethyl)-N-(benzyl)daunorubicin
N-(1-cyano-2-methoxyethyl)-N-(benzyl)doxorubicin
N-cyanomethyl-N-(2-methoxyethyl)daunorubicin
N-cyanomethyl-N-(2-methoxyethyl)doxorubicin
N-cyanomethyl-N-(2-hydroxyethyl)daunorubicin
N-cyanomethyl-N-(2-hydroxyethyl)doxorubicin
N-(1-cyano-2-methoxyethyl)-N-(2-methoxyethyl)daunorubicin
N-(1-cyano-2-methoxyethyl)-N-(2-methoxyethyl)doxorubicin
N-(1-cyano-2-methoxyethyl)-N-(2-hydroxyethyl)daunorubicin
N-(1-cyano-2-methoxyethyl)-N-(2-hydroxyethyl)doxorubicin
N-(α-cyanobenzyl)-N-(2-methoxyethyl)daunorubicin
N-(α-cyanobenzyl)-N-(2-methoxyethyl)doxorubicin
N-(α-cyanobenzyl)-N-(2-hydroxyethyl)daunorubicin
N-(α-cyanobenzyl)-N-(2-hydroxyethyl)doxorubicin
N-(1-cyano-2-methoxyethyl)-N-(4'-anhydro)daunorubicin
N-(1-cyano-2-methoxyethyl)-N-(4'-anhydro)doxorubicin
N-(1-cyano-2-methoxyethyl)-N-(4'-(anhydro)hydroxymethyl)daunorubicin
N-(1-cyano-2-methoxyethyl)-N-(4'-(anhydro)hydroxymethyl)doxorubicin
N-(pyrid-3-yl,cyanomethyl)daunorubicin
N-(pyrid-3-yl,cyanomethyl)doxorubicin (*J Org Chem* (1972) 37:4465)

Additional analogs of the above listed compounds are prepared wherein R of formula 1 is hydrogen, hydroxy, 1–3C alkyl, 1–3C terminal hydroxyalkyl or its ester or ether derivatives, or the ketimine derivatives of the carbonyl-containing embodiments of R, by substituting the appropriate daunosaminylated anthracyclines for daunorubicin or doxorubicin in the foregoing synthesis. Alternate stereochemistries at the 4-C of the daunosamine sugar moiety as set forth above, may also be used.

EXAMPLE 7

Biological Activity Verification

The compounds prepared in Examples 1–5 were tested for in vitro DNA and RNA synthesis inhibition activity and in vivo for ability to increase survival time in mice injected with P-388 leukemia cells as described above. The relative solubility in octanol and phosphate buffer, expressed as $\log_{10} p$, was also determined, as well as the $\Delta T_m$ of isolated helical DNA synthesized in the in vitro test. The results are shown below:

| Compound Tested | L1210 cells inhib of synth, ED$_{50}$, μM | | ΔTm of isolated helical DNA, °C. | log$_{10}$ p, octanol-phosphate buffer at pH 7.4 | Mouse P388 qd 1, % T/C (mg/kg) |
|---|---|---|---|---|---|
| | DNA | RNA | | | |
| Daunorubicin | 0.66 | 0.33 | 10.5 | 0.66 | |
| Doxorubicin | 1.6 | 0.58 | 12.8 | 0.07 | 258 (10) |
| N—(cyanomethyl)-daunorubicin | 1.75 | 0.82 | 11.7 | 2.28 | |
| N—(cyanomethyl)-doxorubicin | 1.2 | 0.29 | 13.9 | 1.20 | |
| N—(1-cyano-2-methoxy-ethyl)daunorubicin | 0.51 | 0.51 | | 2.64 | |
| N—(1-cyano-2-methoxy-ethyl)doxorubicin | 0.80 | 0.40 | 12.5 | | 289 (20) |

We claim:

1. A compound of the formula:

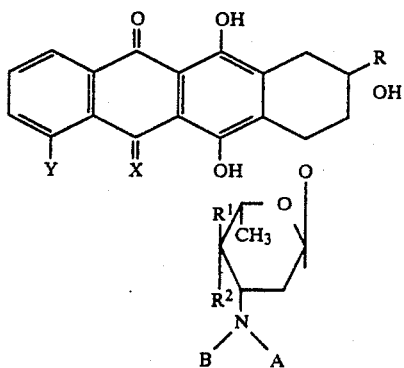

and the pharmaceutically acceptable salts thereof wherein R is:

—CO—CH$_3$, —CHOH—CH$_3$, —CO—CH$_2$OH, —CHOH—CH$_2$OH, hydrogen, hydroxy, 1 to 3 carbon alkyl, 1 to 3 carbon terminal hydroxyalkyl; or, a 2 to 7 carbon ester or diester of said —CO—CH$_2$OH, —CHOH—CH$_2$OH, —CHOH—CH$_3$ or of said 1 to 3 carbon terminal hydroxyalkyl; or said —CO—CH$_2$OH, —CHOH—CH$_2$OH, or —CHOH—CH$_3$ or said 1 to 3 C-terminal hydroxyalkyl having 1 to 6 carbon alkyl or aryl ether replacements of one or more of the hydroxyls; or 13-ketimine derivatives of —CO—CH$_3$ and —CO—CH$_2$OH;

Y is hydrogen, hydroxy, or methoxy,

X is O or NH, but when Y is hydrogen or hydroxy, X must be O;

at least one of R$^1$ and R$^2$ is hydrogen and the other is hydrogen, hydroxy, or methoxy;

B is H, alkyl (1–6) or aryl (6–15) which is unsubstituted or which contains substituents selected from the group consisting of halo, lower alkyl (1–4) nitro or lower alkoxy; lower alkyl (1–4), said alkyl or said unsubstituted or substituted aryl lower alkyl also being unsubstituted or substituted with hydroxy, alkoxy, carbonyl, cyano or ester group substitutions; or B and R$^2$ taken together, in order, are the methylene-oxygen bridge —CH$_2$—O—; and A is —CHR$^3$CN wherein R$^3$ is H, aryl (6–15), which is unsubstituted or which contains substituents selected from the group consisting of halo, lower alkyl (1–4) nitro or lower alkoxy; alkyl (1–6) or aryl lower alkyl (1–4), wherein the aryl is unsubstituted or contains substituents selected from the group consisting of halo, lower alkyl (1–4) nitro or lower alkoxy; said alkyl or aryl lower alkyl is unsubstituted or contains hydroxy, alkoxy, carbonyl, or ester group substitutions.

2. The compound of claim 1 wherein R is COCH$_3$, CHOHCH$_3$, COCH$_2$OH, or CHOHCH$_2$OH.

3. The compound of claim 2 wherein Y is hydrogen, R$^1$ is hydrogen, and R$^2$ is OH or R$^2$ and B taken together in order are the methylene oxygen bridge —CH$_2$—O—.

4. The compound of claim 2 wherein B is H or CHR$^3$CN.

5. The compound of claim 4 which is selected from the group consisting of

N-(cyanomethyl)daunorubicin, N(cyanomethyl)doxorubicin,

N-(1-cyano-2-methoxyethyl)daunorubicin and

N-(1-cyano-2-methoxyethyl)doxorubicin.

* * * * *

UNITED STATES PATENT AND TRADEMARK OFFICE
CERTIFICATE OF CORRECTION

PATENT NO. : 4,591,637

DATED : 27 May 1986

INVENTOR(S) : Edward M. Acton et al

It is certified that error appears in the above-identified patent and that said Letters Patent is hereby corrected as shown below:

In claim 1:

Column 12, line 19

After "aryl (6-15)" delete "which" and substitute --lower alkyl (1-4) wherein said aryl--

Column 12, line 20

After "or" delete "which"

Column 12, line 22

After "lower alkoxy", delete "; lower alkyl (1-4)"

Lines 19-26 should now read:

B is H, alkyl (1-6) or aryl (6-15) lower alkyl (1-4) wherein said aryl is unsubstituted or contains substituents selected from the group consisting of halo, lower alkyl (1-4) nitro or lower alkoxy, said alkyl or said unsubstituted or substituted aryl lower alkyl also being unsubstituted or substituted with hydroxy, alkoxy, carbonyl, cyano or ester group substitutions; or Signed and Sealed this Thirteenth Day of September, 1988

*Attest:*

DONALD J. QUIGG

*Attesting Officer*   *Commissioner of Patents and Trademarks*